(12) United States Patent
To et al.

(10) Patent No.: US 11,662,395 B1
(45) Date of Patent: May 30, 2023

(54) SOAK TESTER APPARATUS AND SYSTEM

(71) Applicant: Neuralink Corp., Fremont, CA (US)

(72) Inventors: John W. F. To, Castro Valley, CA (US); Srinivasan Ramakrishnan, Fremont, CA (US); Julian Borrey, Fremont, CA (US); Russell Ohnemus, San Francisco, CA (US); Joshua S. Hess, Dublin, CA (US); Robin E. Young, San Francisco, CA (US); Sonal Pinto, San Bruno, CA (US)

(73) Assignee: NEURALINK CORP., Fremont, CA (US)

( * ) Notice: Subject to any disclaimer, the term of this patent is extended or adjusted under 35 U.S.C. 154(b) by 0 days.

(21) Appl. No.: 17/536,739

(22) Filed: Nov. 29, 2021

(51) Int. Cl.
*G01R 31/54* (2020.01)
*G01R 27/16* (2006.01)
*A61N 1/05* (2006.01)
*A61B 5/25* (2021.01)

(52) U.S. Cl.
CPC ............ *G01R 31/54* (2020.01); *G01R 27/16* (2013.01); *A61B 5/25* (2021.01); *A61N 1/05* (2013.01)

(58) Field of Classification Search
CPC .......... G01R 31/54; G01R 27/16; A61B 5/25; A61B 1/05
See application file for complete search history.

(56) References Cited

U.S. PATENT DOCUMENTS

| | | | |
|---|---|---|---|
| 11,198,006 B1* | 12/2021 | Nijlunsing | A61N 1/36062 |
| 2006/0265024 A1* | 11/2006 | Goetz | A61N 1/3706 607/48 |
| 2014/0327460 A1* | 11/2014 | Zhou | A61N 1/372 324/750.03 |
| 2018/0338765 A1* | 11/2018 | Judy | A61L 31/028 |
| 2021/0387001 A1* | 12/2021 | Martens | A61N 1/0551 |

FOREIGN PATENT DOCUMENTS

WO    WO-2020206332 A1 * 10/2020 ......... A61N 1/37223

OTHER PUBLICATIONS

N Donaldson et al. Apparatus to investigate the insulation impedance and accelerated life-testing of neural interfaces 2018 J. Neural Eng. 15 066034.*

\* cited by examiner

*Primary Examiner* — Christopher E Mahoney
(74) *Attorney, Agent, or Firm* — Kilpatrick Townsend & Stockton LLP

(57) ABSTRACT

The disclosure provides a soak tester apparatus for testing an implantable enclosure having an impedance engine, a multiplexer and a removably attached cartridge, which cartridge has a plurality of threads, comprising a Faraday cage housing; a receptacle disposed within the Faraday cage housing, wherein the receptacle is configured to host an implantable enclosure having an impedance engine, a multiplexer and a removably attached cartridge, which cartridge has a plurality of threads; and a pigtail disposed within the Faraday cage housing having a charging coil configured to power the implantable enclosure.

21 Claims, 8 Drawing Sheets

SOAK TESTER APPARATUS AND SYSTEM

BACKGROUND

Implantable devices with electrodes can be used for recording and stimulating electrical signals in target biological tissue, such as the brain. However, during implantation the electrodes can damage or inflame the biological tissue, complicating an accurate study, diagnosis, and/or medical treatment of the tissue. Moreover, an immune response as well as growth of the tissue around the implantation site may degrade the long term viability and stability of implanted electrodes.

U.S. Patent App. Pub. No.: 2020/0085375 to Tolosa discloses biocompatible multi-electrode arrays capable of being implanted in sensitive tissue, such as the brain, and methods for fabricating such arrays. The disclosed arrays can be implanted in living biological tissue with a single needle insertion. The devices can include linear arrays with contacts along an edge, linear arrays with multiple electrodes per opening in a polyimide support layer, multi-thread electrode arrays, tree-like electrode arrays, and the like.

U.S. Patent App. Pub. No.: 2020/0086111 to Young discloses a system and method for implanting devices into biological tissue (e.g., brain tissue). The system may include a biocompatible probe, an integrated circuit (IC) chip tethered to the probe, a cartridge comprising a temporary attachment surface by which the probe is removably coupled to the cartridge and a fastener for removably coupling the IC chip to the cartridge, a needle to reversibly engage with the probe, a robotic arm to hold the needle, a camera, and a microprocessor controller.

WO2021/011401 to Seo discloses a brain-machine interface (BMI) which includes many flexible electrodes for implanting within a subject's brain and connect to a cylindrical sensor device configured to fit inside the cranium. The device contains sealed electronics that convert analog neural voltages to digital signals, or vice versa, and connects through a serial cable to a subcutaneous relay on the mastoid region (behind the subject's ear) or other suitable location. The relay draws power from and communicates with an externally worn device and distributes the power to the devices. The externally worn device communicates wirelessly or through a tether to a base station computer for data analysis and/or stimulation.

With the advent of implantable probes arrays, test devices are required to ensure the probes have electrical integrity before implantation into a subject. The present disclosure satisfies this need and offers other advantages as well.

BRIEF SUMMARY

An implantable medical device may have a multitude of channels containing probes or threads. During manufacturing and assembly, there is a possibility of mechanical damage to the threads, damage to an electrode coating material such as sputtered iridium oxide films (SIROF), or damage to the thin film electrodes themselves. These types of damage can lead to different failure modes, including damage to the metal traces (wires) and polyimide insulation, the loss of electrode coating material and the mechanical integrity of the electrode materials.

A high percentage of intact threads are required for a successful implant surgery, as the bandwidth of the device is defined by the number of functional channels, which directly influences performance. As such, in one embodiment, the present invention provides a soak tester apparatus for testing an implantable enclosure having an impedance engine, a multiplexer and a removably attached cartridge, which cartridge has a plurality of threads. In certain instances, the removably attached cartridge having a plurality of threads comprises a temporary attachment surface for each of the threads. Each of the plurality of threads is tethered to the implantable enclosure. The soak tester apparatus can ensure that the plurality of threads are intact and ready to be surgically implanted. The soak tester apparatus comprises:
- a Faraday cage housing;
- a receptacle disposed within the Faraday cage housing, wherein the receptacle is configured to host an implantable enclosure having an impedance engine, a multiplexer and a removably attached cartridge, which cartridge has plurality of threads; and
- a pigtail disposed within the Faraday cage housing having a charging coil configured to power the implantable enclosure, wherein the impedance engine and the multiplexer allow a 2-point electrical characteristic measurement of each of the plurality of threads.

In certain aspects, the measured electrical characteristic of each of the plurality of threads is impedance.

In another embodiment, the present disclosure provides a method for measuring an electrical characteristic of an implantable enclosure having an impedance engine, a multiplexer and a removably attached cartridge, which cartridge has a plurality of threads, the method comprising:
- placing an implantable enclosure having an impedance engine, a multiplexer and a removably attached cartridge, which cartridge has a plurality of threads into a soak tester apparatus, the apparatus comprising a receptacle disposed within a Faraday cage housing, wherein the receptacle is configured to host the removably attached cartridge;
- connecting a pigtail disposed within the Faraday cage housing having a charging coil configured to power the implantable enclosure, wherein the impedance engine and the multiplexer allow a 2-point electrical characteristic measurement of each of the plurality of threads; and
- measuring the 2-point electrical characteristic of each of the plurality of threads to assess the integrity of each of the plurality of threads.

In certain aspects, the measured electrical characteristic of each of the plurality of threads is impedance.

In still yet another embodiment, the present disclosure provides a system for testing an implantable enclosure having an impedance engine, a multiplexer and a removably attached cartridge, which cartridge has a plurality of threads, the system comprising:
i) a soak tester apparatus comprising a Faraday cage housing;
ii) a receptacle disposed within the Faraday cage housing, wherein the receptacle is configured to host an implantable enclosure having an impedance engine, a multiplexer and a removably attached cartridge, which cartridge has a plurality of threads; and
iii) a pigtail disposed within the housing having a charging coil configured to power the implantable enclosure, wherein the impedance engine and the multiplexer allow a 2-point electrical characteristic measurement of each of the plurality of threads;
v) at least two reservoirs; and
vi) a computing system comprising a computer program product, which includes executable program code for a method of testing an implantable enclosure.

In certain aspects, the measured electrical characteristic of each of the plurality of threads is impedance.

These and other objects, aspects and embodiments will become more apparent when read with the detailed description and figures which follow.

BRIEF DESCRIPTION

FIG. 1 is an illustration of a soak tester apparatus of the disclosure.

FIG. 2A-B illustrate an embodiment of an implantable enclosure being soaked. FIG. 2B is an expanded view of a portion of FIG. 2A.

FIG. 7 is an illustration of an embodiment of the disclosure.

DETAILED DESCRIPTION

Figure 1:
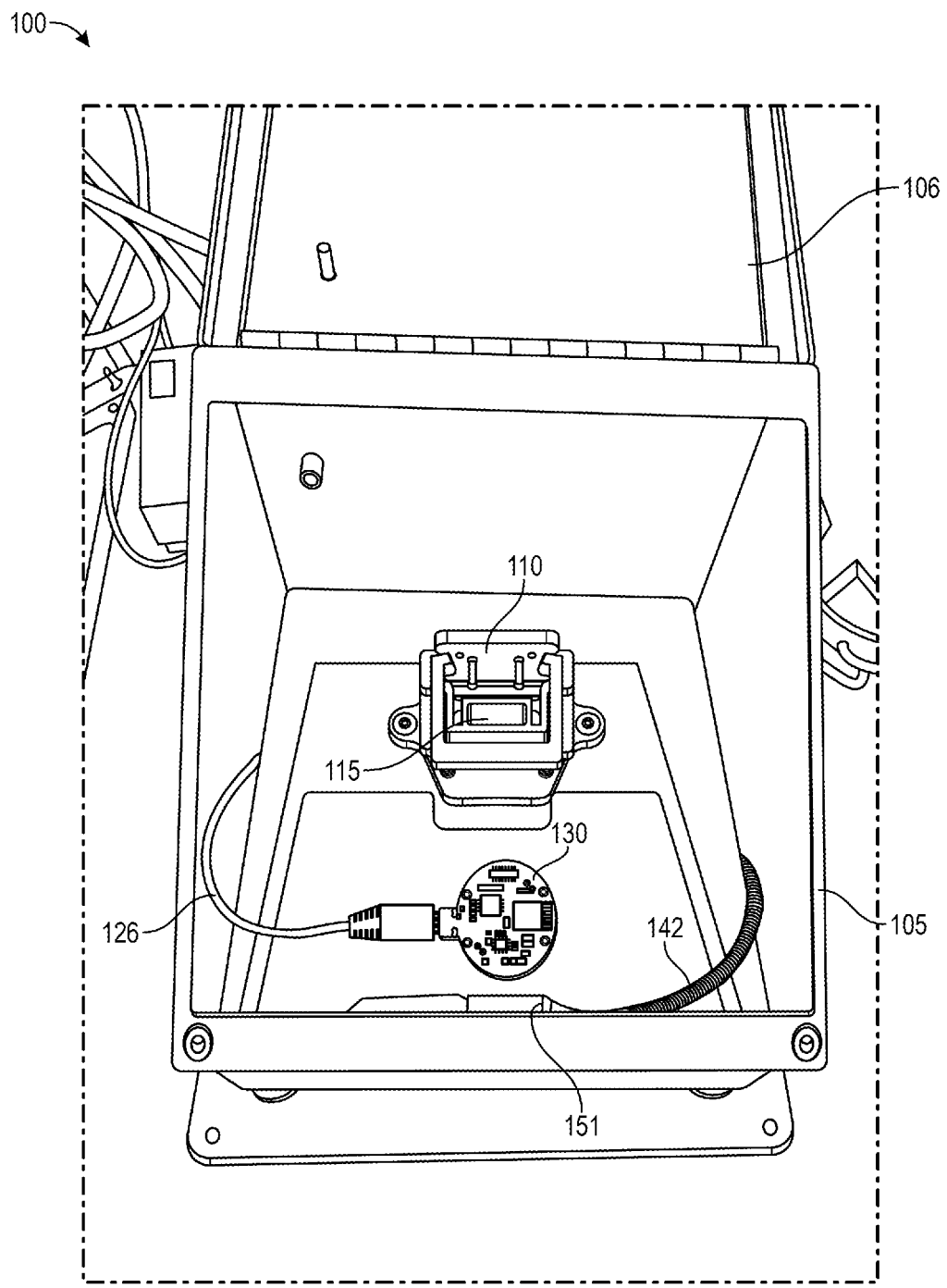

In one embodiment, the present disclosure provides an apparatus 100 as shown in FIG. 1. The soak tester apparatus 100 is useful for testing an electrical characteristic of an implantable enclosure. Typically, the implantable enclosure has an impedance engine, a multiplexer and a removably attached cartridge, which cartridge has a plurality of threads. In certain instances, the removably attached cartridge having a plurality of threads comprises a temporary attachment surface for each of the threads. Each of the plurality of threads is tethered to the implantable enclosure.

The soak tester apparatus 100 comprises a Faraday cage housing 105 with a lid 106. A Faraday cage is a protective shield against electromagnetic radiation coming from the external environment, or it prevents or reduces electromagnetic energy radiated from the internal components from escaping the cage. Disposed within the housing is a receptacle 110 configured to host an implantable enclosure. A slot 115 at the center allows threads on the cartridge to soak in a salt solution while an electrical measurement(s) is performed. Afterwards, the threads are washed with plentiful DI water to remove any salt residue and crystals on the threads and electrodes. A pigtail 130 is also disposed within the housing. Pigtail 130 comprises an inductive charging coil. Connection 126 is a power cable to pigtail 130 having an inductive charging coil. Connection 142 is a cable connected to a Bluetooth dongle 151 that allows data to be transmitted wirelessly between the implantable enclosure and a computer. The inductive charger 130 charges the battery in the implantable enclosure and powers the impedance engine and the multiplexer. The implantable enclosure contains an on-board impedance engine configured to supply an electrical signal to each of the plurality of threads. The soak tester is useful for testing an electrical characteristic of each of the plurality of threads on the cartridge. The impedance engine and the multiplexer allow a 2-point electrical characteristic measurement of each of the plurality of threads.

In certain aspects, the removably attached cartridge comprises a temporary attachment surface by which the plurality of threads are each removably coupled to the cartridge and a fastener for removably coupling the implantable enclosure to the cartridge. Further, the implantable enclosure tethers each of the plurality of threads. During surgery, a robotic arm configured to hold a needle, removes each of the plurality of threads from the temporary attachment surface of the cartridge, pierces a biological tissue with the needle and a thread, withdraws the needle while leaving the thread within the biological tissue, and leaves the implantable enclosure with the biological tissue, with the implantable enclosure still tethered to each of the plurality of threads. The cartridge is then removed by decoupling from the implant enclosure.

In certain aspects, an electrical characteristic of each of the plurality of threads is a measured parameter of continuity or integrity of the electrical path between each of the plurality of threads and the impedance engine. The measured parameter can be for example, an electrical parameter such as impedance, voltage, amperage or a combination thereof. In certain aspects, the electrical characteristic is a 2-point impedance measurement of the nearest neighbor pairs of the plurality of threads.

In certain instances, the measured parameter is impedance using alternating current. The range of impedance can be from 50 Hz to 5000 Hz, such as 500 Hz to 2000 Hz. In certain instances, the impedance measured using alternating current is an impedance of about 1000 Hz. Impedance measurements can be collected with a driving voltage of about a 600 mV to about 5 V at frequencies ranging from 50 Hz to 5000 Hz. In certain aspects, the input voltage is about 75 mV to about 150 mV such as about 100 mV. In certain aspects, the impedance measurement is a small perturbation of input voltage.

In certain instances, the receptacle 110 within the housing comprises a slot 115 for holding a liquid bath. The slot is configured to host the plurality of threads from an implantable enclosure.

In certain instances, the slot 115 of the receptacle comprises a liquid. The liquid can be a high ionic strength salt solution such as about 0.1M to about 1M, such as a concentration of for example, 0.1, 0.2, 0.3, 0.4, 0.5, 0.6, 0.7, 0.8, 0.9 or about 1.0 M. In certain instances, the solution can be physiological saline, phosphate buffered saline, or artificial cerebrospinal fluid (aCSF), organic-substance-free acellular simulated body fluid (SBF), or a non-buffered neutral pH salt solution such as, sodium chloride or potassium chloride. The salt solution can be potassium nitrate. In certain instances, the pH value of the salt solution is neutral or about pH=6.0 to about 8.0, or about pH=7.0.

The salt solution, such as a $KNO_3$ electrolyte solution, facilitates an ionic path between a counter electrode and a working electrode on the threads to allow electrochemical impedance spectroscopy measurements to take place.

In certain instances, the implantable enclosure having an impedance engine, a multiplexer and a removably attached cartridge is a brain-machine interface (BMI) implant. In certain instances, the implantable enclosure contains custom, low-power integrated circuit (IC) chips for on-board amplification and digitization. The implantable enclosure gathers data from threads comprising flexible electrodes that can be implanted into a brain of a subject. The threads are implanted via assistance from a neurosurgical robot. An intact thread is a requirement for a successful implant surgery.

In some aspects, the removably attached cartridge having a plurality of threads comprises a temporary attachment surface for each of the threads. The attachment surface can be formed of one or more of polyimide or silicon and the cartridge further comprises an adhesive layer beneath the temporary attachment surface. In some aspects, each thread includes an electrode configured to be inserted into biological tissue and a receiving feature mounted on the cartridge for engagement with an insertion needle. Each thread remains tethered to the implantable enclosure.

The removably attached cartridge is used to guide implantation of one or more of the plurality of threads. Each thread is coupled to the implantable enclosure. The implantable enclosure holds electronics such as one or more circuits which are protected (e.g., hermetically sealed) by the structure. The cartridge may be removably attached to the thread and/or implantable enclosure. "Removably attached" or "removably coupled" may refer to components that are attached and can be detached relatively easily. For example, magnetically attached components, and components snapped together via mechanical attachments that are loosened with a simple motion, are removably attached.

Once implanted and in operation, electrical signals within a subject's brain are picked up by implanted thin-film electrodes and transported to the implantable enclosure set in a burr hole of the subject's skull. The implantable enclosure includes amplifiers, analog-to-digital converters (ADC), multiplexing electronics, and impedance engine to turn the brain signals into timestamped, serialized digital packets.

Figure 2A:
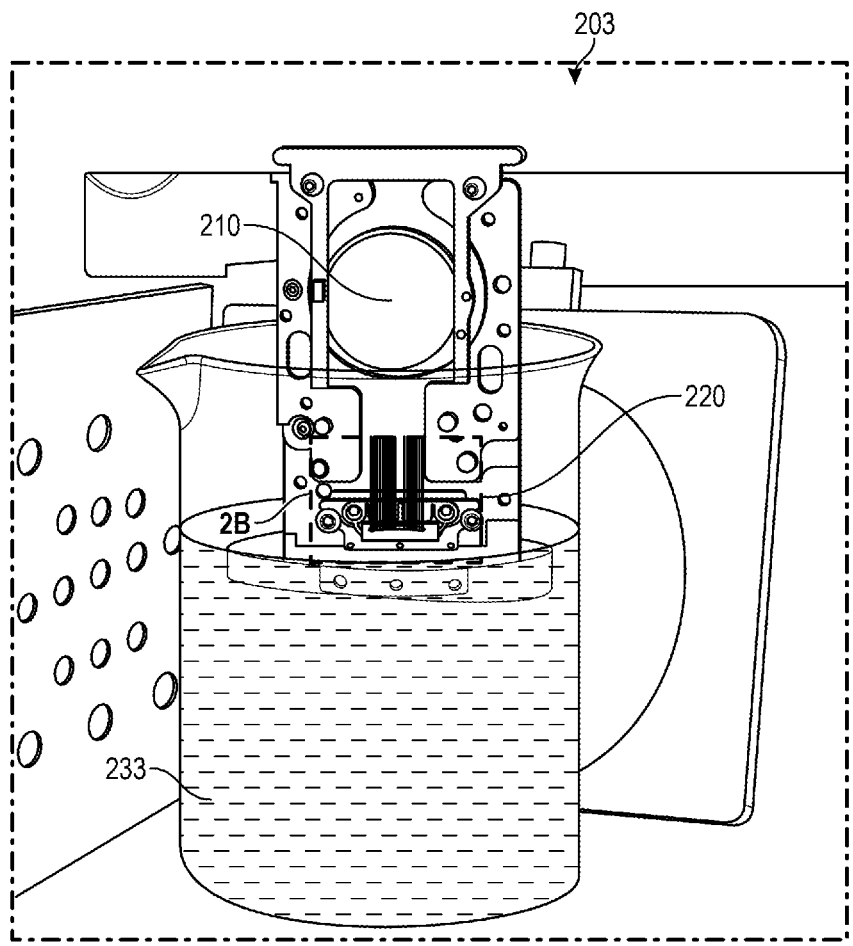

In certain instances, the removably attached cartridge having a plurality of threads is tested in the apparatus of this disclosure prior to surgery. A "thread" is a lithographically formed conductor surrounded by an insulator. The testing apparatus ensures electrical integrity of the plurality of threads. FIG. 2A shows an implantable enclosure 210 being placed into a beaker 233 of potassium nitrate solution and disposed within a removable implant frame 203. Implant frame 203 is used to align implant enclosure 210 onto a burr hole of the cranium of a subject. After the implant enclosure 210 is surgically inserted, the frame 203 is removed. Box 220 is enlarged to show the plurality of threads as in FIG. 2B, wherein the bottom 5 mm of the threads is soaked inside a beaker filled with salt solution.

Figure 2B:
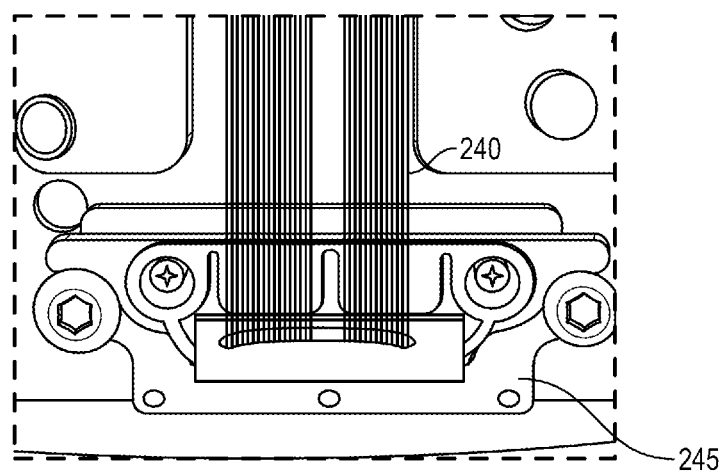

Turning now to FIG. 2B, the cartridge 245 clearly shows a plurality of threads 240. The flexible threads 240 exit cartridge 245, and once implanted, the polymer-embedded electrodes (not shown) attached to the threads descend into the brain of the subject. In certain aspects, the implantable enclosure is a silicone- or polymer-casted package that is molded into a cylindrical puck with a thin film of threads emerging from one end. Inside the puck is a hermetic glass or other biocompatible material package containing electronics and thin film attached through vias or otherwise to a custom system on a chip (SoC). Each thread is tethered to the implant enclosure.

In another embodiment, the disclosure provides a system for testing an implantable enclosure having an impedance engine, a multiplexer and a removably attached cartridge, which cartridge has a plurality of threads, the system comprising:
 a soak tester apparatus as described herein;
 at least two reservoirs; and
 a computing system comprising a computer program product, which includes executable program code for a method of testing an implantable enclosure.

Figure 3:
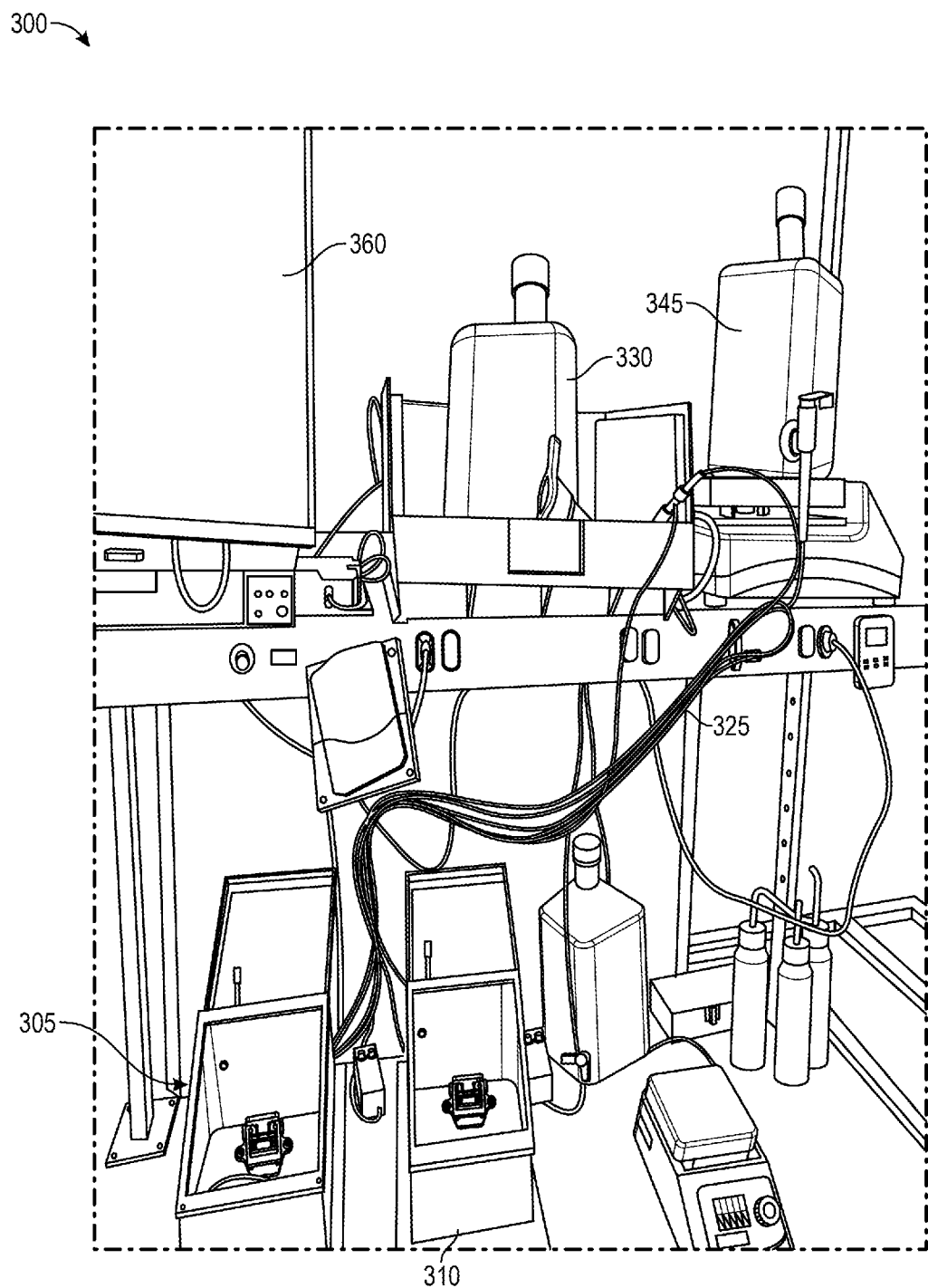
FIG. 3 is an illustration of an embodiment of the disclosure showing an array of the soak tester apparatuses of the disclosure.

FIG. 3 shows a system 300 of this disclosure for testing an implantable enclosure. In certain aspects, the system can include an array of soak testing apparatuses (two or more) (305, 310) for example, one or more soak testing apparatuses (305, 310). In certain instances, the system contains only one soak testing apparatus. The system includes at least two reservoirs 330 and 345. The first reservoir 330 is configured to hold a liquid such as a high ionic strength salt solution for electrical measurements. The second reservoir 345 is configured to hold deionized (DI) or distilled water. After the electrical measurements, the threads are washed with water to remove any salt residue and crystals on the threads and electrodes. In certain other aspects, the first reservoir holds water and the second reservoir holds a high ionic strength solution. The reservoirs are each fluidly connected 325 to the soak testing apparatuses 305, 310.

The soak tester apparatus and system allow a multitude of threads to be soaked in an electrolyte solution such as potassium nitrate ($KNO_3$). Other salts are suitable for use in the present disclosure. The choice of the electrolyte is based on the high ionic strength of the potassium nitrate salt. Measurements are performed to ensure proper tested impedance of all the threads using the testing device.

System 300 comprises a computing system which includes one or more microprocessors/processing devices that is a component of the system. Custom software configurations can be used. The computing system 360 comprises a computer program product, which includes executable program code for a method of testing an implantable enclosure. The system further includes a display interface and/or operational controls configured to be handled by a user to monitor the soak testing system, to change configurations of the system, and to operate, directly guide, or set programmed instructions for the system, and sub-portions thereof. Such processing devices can be communicatively coupled to a non-volatile memory device via a bus. The non-volatile memory device may include any type of memory device that retains stored information when powered off.

Within each implantable enclosure is circuitry, including integrated circuit (IC) chips, capacitors, and other components. The ICs receive from, and/or transmit to, the threads comprising thin film electrodes that are surgically implanted within the subject's cranium. The ICs can include analog-to-digital converters (ADC) and/or digital-to-analog converters (DAC) in order to convert analog signals in the brain to or from digital signals of a computer. The IC chips that include the ADCs can also include multiplexers/demultiplexers that multiplex digital signals together to put on the serial cable, or demultiplex serial signals from the serial cable apart for output to the DACs. The former is for reading out from the brain, while the latter is for stimulating the brain.

Sitting in the burr hole of a cranium, within the biocompatible/implantable enclosure, are a tight pack of electrical components. The components are carefully positioned to interface with the thin film ribbon cable of what may be thousands of individual, electrically isolated metal trances leading to electrodes inserted into the brain. The threads (16 traces to a thread) and electrodes are manufactured using microelectromechanical systems (MEMS) technologies. The threads are manufactured monolithically with a standard silicon wafer substrate and connect with electrodes. Each electrode site is oval and has a geometric surface area of ~370 $\mu m^2$ that is coated with a high surface area material. In the exemplary embodiment, each implantable enclosure has 1,024 channels, with 64 threads of 16 electrodes each. Every channel supports both stimulation and recording. In one aspect, the implantable enclosure physical package is an 8 mm cylindrical "puck" that fits into an 8 mm drilled burr hole to sit flush with the surface of the skull of a subject.

Figure 4:
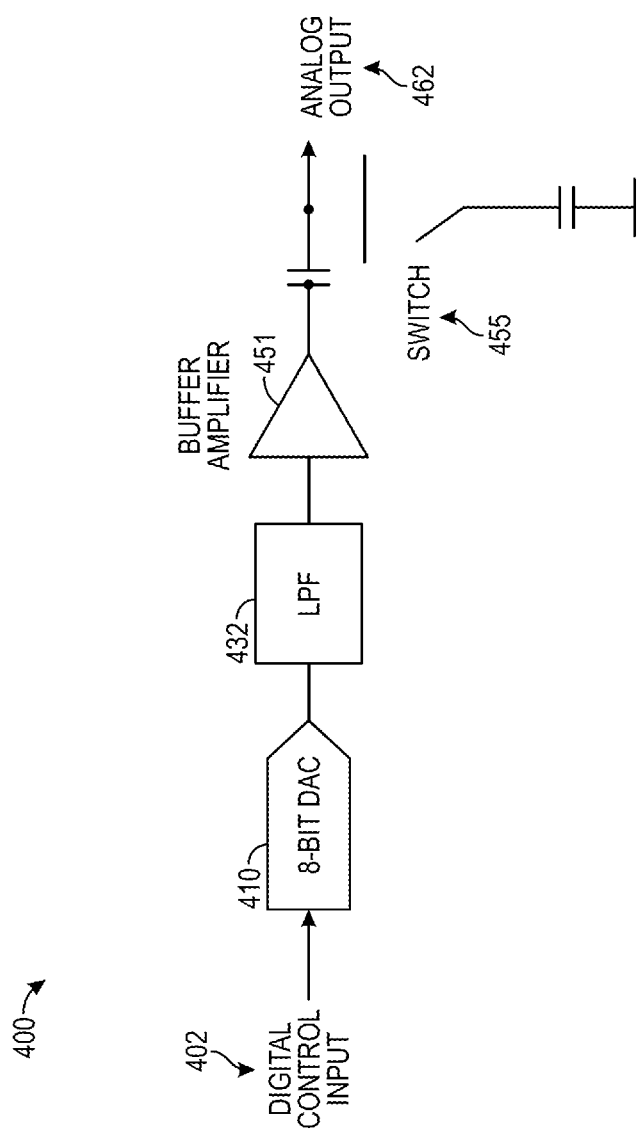
FIG. 4 is an illustration of an impedance engine of the disclosure.

In certain aspects, the implantable enclosure has an on-board impedance engine for the frontend of impedance measurements. As shown in FIG. 4, an on-board impedance engine or circuit 400 contains a digital controller 402 providing digital control input into a digital to analog converter 410. The D/A converter converts digital data into an analog signal, which D/A converter can range from 8 bits to 24 bits. The analog signal passes through a low pass filter 432 for low noise levels and then a buffer amplifier 451. The buffer amplifier 451 buffers the output of the filter and provides low impedance drive and absorbs transient currents. After the analog signal is filtered and buffered, the analog signal is output 462 when switch 455 is switched on or is connected to the circuit. When the switch is on, the impedance engine 400 produces an analog signal output that emulates tissue impedance. When the switch is switched off, or disconnected to the impedance engine, the electrodes can be implanted into tissue (brain tissue).

Figure 5:
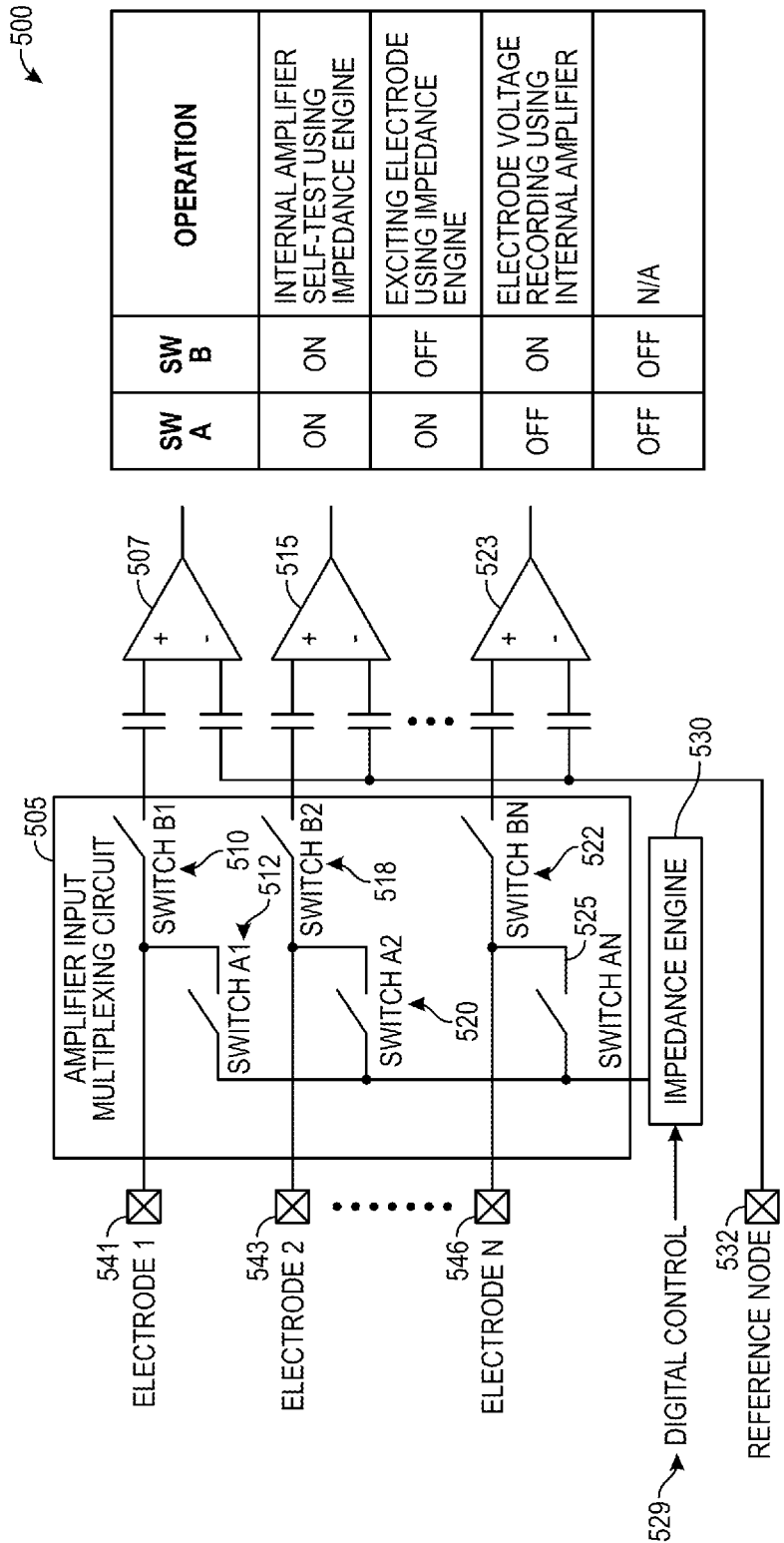
FIG. 5 is an illustration of a multiplexer system of the disclosure.

In addition to the on-board impedance engine, the implant enclosure also contains a multiplexer, and a plurality of threads comprising electrodes. A multiplexing system 500 is shown in FIG. 5. Impedance mapping can be performed using the impedance engine 530 and the multiplexing system 500. The impedance engine 530 supplies an analog signal to the multiplexer 505. Each electrode (541, 543, 546) in the plurality of threads can be individually connected using the multiplexer. This multiplexing system 500 allows two-point impedance measurements by connecting a working electrode (e.g., 541) to the circuit along with the counter electrode or reference node 532. The multiplexer allows any electrode in the plurality of threads to be selected. For example, electrode 541 is selected when switch-B1 510 is connected to a low-noise amplifier (or differential op-amp) 507 (with a capacitors between the electrode 541 and amplifier 507 and a capacitor between reference node 532 and amplifier 507) and switch-A1 512 is connected to the impedance engine. In operation, when switch-A1 512 and switch-B1 510 are both switched on, the system is in a self-testing mode using the on-board impedance engine. When switch-A1 512 is switched on and switch-B1 510 is switched off, the electrode 541 is excited using the impedance engine. When switch-A1 512 is switched off and switch-B1 510 is switched on, the electrode 541 voltage/impedance is recorded.

In certain instances, the impedance measurement methods include applying a small excitation signal from the impedance engine 530 and measuring the response signal. The three-electrode electrochemical cell containing the electrolyte solution enables the multiplexing system 500 to establish an electrical connection with the surface of each of the electrodes. The impedance is determined by measuring the amplitude and phase of the impedance response that occurs with the small excitation signal.

In the three-electrode cell system of the present disclosure, the reference electrode is used to accurately determine the potential, as all the potential measurements in the system are measured with respect to the reference electrode. Impedance is measured between the reference electrode and working electrode (sense), which allows potential changes of the working electrode to be measured. In certain instances, impedance is measured with the driving voltage at frequencies of for example, 50 Hz to 5000 Hz or 500 Hz to 2000 Hz, for the whole frequency band, separated by decades of intervals. No or low signal implies low impedance, whereas high or maximum signal implies large impedance. The measurement and analysis obtained allows for a multi-frequency impedance map.

In yet another embodiment, the present disclosure provides a method for measuring a characteristic of an implantable enclosure having an impedance engine, a multiplexer and a removably attached cartridge, which cartridge has a plurality of threads, the method comprising:

placing an implantable enclosure having an impedance engine, a multiplexer and a removably attached cartridge, which cartridge has a plurality of threads into a soak tester apparatus, the apparatus comprising a receptacle disposed within a Faraday cage housing, wherein the receptacle is configured to host the removably attached cartridge;

connecting a pigtail disposed within the Faraday cage housing having a charging coil configured to power the implantable enclosure, wherein the impedance engine and the multiplexer allow a 2-point electrical characteristic measurement of each of the plurality of threads; and measuring the 2-point electrical characteristic of each of the plurality of threads to assess the integrity of each of the plurality of threads.

In certain instances, the characteristic of each of the plurality of threads is a measured parameter of continuity or integrity of the electrical path between each of the plurality of threads and the impedance engine.

In certain instances, the measured parameter is selected from the group consisting of impedance, voltage or amperage.

In certain instances, the measured parameter is impedance.

In certain instances, impedance is measured in the range of 50 Hz to 5 kHz.

In certain instances, wherein impedance is measured in the range of 500 Hz to 2 kHz.

In certain instances, the receptacle within the housing comprises a slot for holding a liquid bath.

In certain instances, the slot is configured to host the plurality of threads.

In certain instances, the slot further comprises a liquid.

The apparatuses, systems and methods of the present disclosure can be used in a subject such as mammals, rodents (e.g., mice, rats), ungulates, cows, sheep, pigs, horses, non-human primates, and humans.

Figure 6:
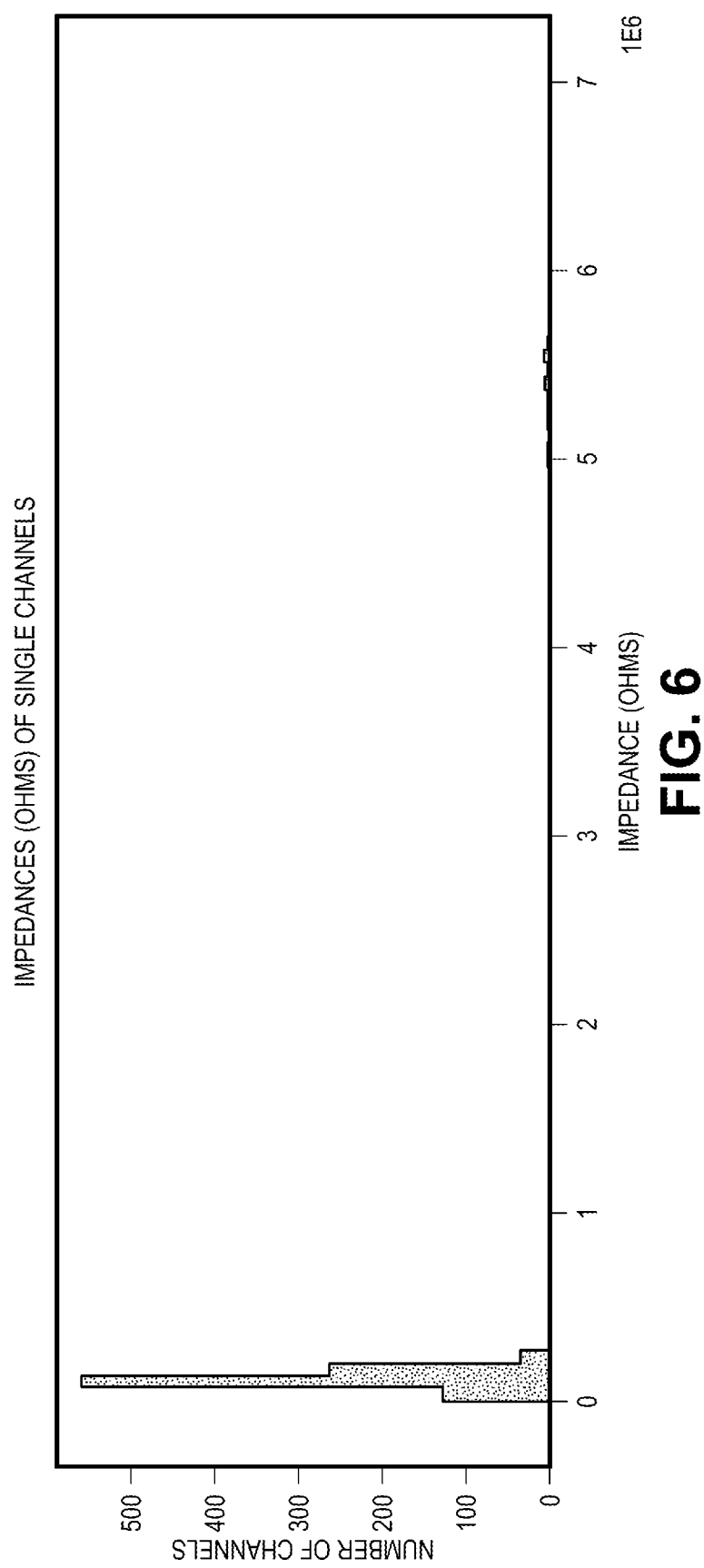
FIG. 6 is an illustration of an embodiment of the disclosure.

In certain instances, all the channels of the implant can be measured. As shown in FIG. 6, in an implant enclosure having 1024 channels all 1024 channels can be measured. The histogram of FIG. 6 shows impedances of all 1024 channels measured. FIG. 6 shows impedance measurement when the traces are not in contact with an electrolyte, therefore their readings are all in the higher end of the impedance spectrum. In certain instances, a cutoff value can be applied to the above histogram to determine the amount of "good" electrodes and the overall yield of the electrodes.

In one exemplary embodiment, a threshold of 80% of the threads having an acceptable impedance measurement is sufficient for implantation. In one instance, the plurality of threads has 64 threads of 16 electrodes each. In this manner, 49-52 threads such as 49, 50, 51 or 52 threads having the proper impedance will be sufficient for surgery.

Figure 7:
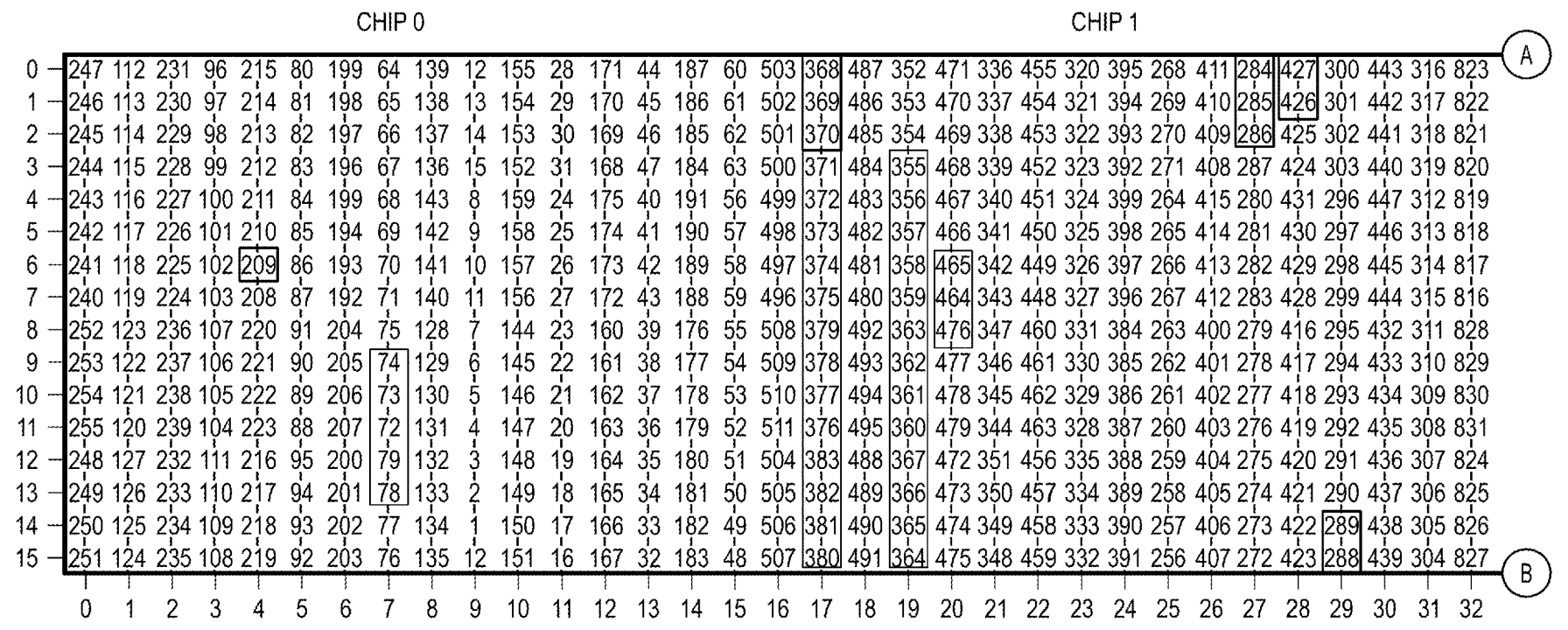
Figure 7:
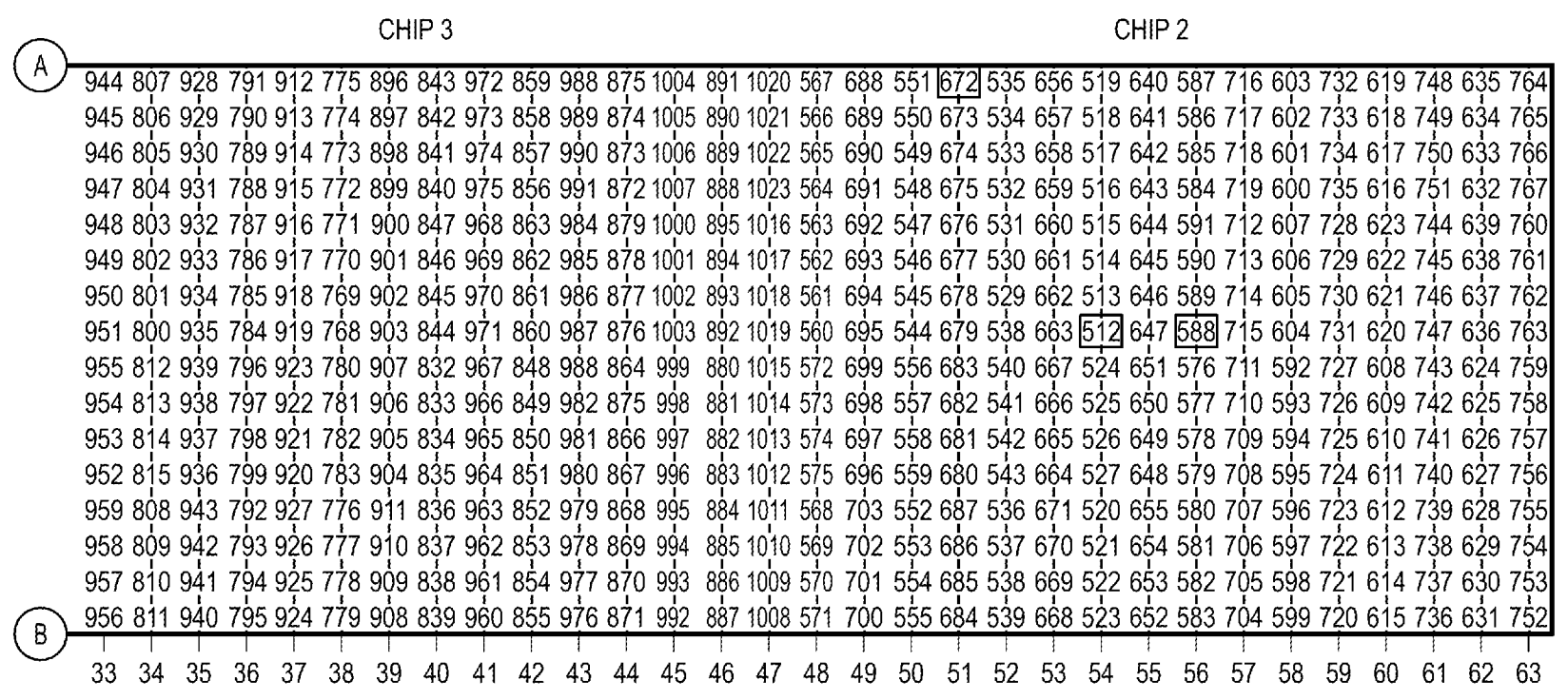

FIG. 7 shows a heat map of impedance representing 0 to 6 MΩ ($10^6$ ohms) using the system of the present disclosure. The system permits two-point impedance measurements by multiplexing to each individual electrode and the counter electrode.

The tabulation of coupling ratios C_XY in FIG. 7 shows the amplitude of the oscillation seen on channel X vs channel Y, when driving a waveform on channel Y. The ratio determines the amount of cross-coupling between channel X and channel Y. This ratio provides information about shorts present between the channels either through metallic shorts from the metal traces due to defects formation in the fabrication process or the solder joint short formation due to imperfection in the assembly process. The coupling ratio measurement of neighboring electrodes is useful to indicate failure rate. The boxed values indicate that each of the 1024 channels is measured and evaluated.

As used in the disclosure, non-limiting examples of the memory devices include electrically erasable programmable read-only memory ("ROM"), flash memory, or any other type of non-volatile memory. In some aspects, at least some of the memory device can include a non-transitory medium or memory device from which the processing device can read instructions. A non-transitory computer-readable medium can include electronic, optical, magnetic, or other storage devices capable of providing the processing device with computer-readable instructions or other program code. Non-limiting examples of a non-transitory computer-readable medium include (but are not limited to) magnetic disk(s), memory chip(s), ROM, random-access memory ("RAM"), an ASIC, a configured processor, optical storage, and/or any other medium from which a computer processor can read instructions. The instructions may include processor-specific instructions generated by a compiler and/or an interpreter from code written in any suitable computer-programming language, including, for example, C, C++, C#, Java, Python, Perl, JavaScript, etc.

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references cited in this application, including patent applications, patents, and PCT publications, are incorporated herein by reference for all purposes.

What is claimed is:

1. A soak tester apparatus for testing an implantable enclosure having an impedance engine, a multiplexer and a removably attached cartridge, which cartridge has a plurality of threads, the soak tester apparatus comprising:
   a Faraday cage housing;
   a receptacle disposed within the Faraday cage housing, wherein the receptacle is configured to host an implantable enclosure having an impedance engine, a multiplexer and a removably attached cartridge, which cartridge has a plurality of threads; and
   a pigtail disposed within the Faraday cage housing having a charging coil configured to power the implantable enclosure, wherein the impedance engine and the multiplexer allow a 2-point electrical characteristic measurement of each of the plurality of threads.

2. The apparatus of claim 1, wherein the characteristic measurement of each of the plurality of threads is a measured parameter of continuity of the electrical path between each of the plurality of threads and the impedance engine.

3. The apparatus of claim 2, wherein the measured parameter is selected from the group consisting of impedance, voltage and amperage.

4. The apparatus of claim 3, wherein the measured parameter is impedance.

5. The apparatus of claim 4, wherein impedance is measured with an alternating current between 50 Hz to 5,000 Hz.

6. The apparatus of claim 4, wherein impedance is measured with an alternating current in the range of 500 Hz to 2000 Hz.

7. The apparatus of claim 1, wherein the receptacle within the Faraday cage housing comprises a slot for holding a liquid bath.

8. The apparatus of claim 7, further comprising a liquid.

9. The apparatus of claim 7, wherein the liquid is of high ionic strength.

10. The apparatus of claim 1, wherein the slot is configured to host the plurality of threads.

11. A system for testing an implantable enclosure, the system comprising:
    a soak tester apparatus of claim 1;
    at least two reservoirs; and
    a computing system comprising a computer program product, which includes executable program code for a method of testing an implantable enclosure.

12. A method for measuring a characteristic of an implantable enclosure having an impedance engine, a multiplexer and a removably attached cartridge, which cartridge has a plurality of threads, the method comprising:
    placing an implantable enclosure having an impedance engine, a multiplexer and a removably attached cartridge, which cartridge has a plurality of threads into a soak tester apparatus, the apparatus comprising a receptacle disposed within a Faraday cage housing, wherein the receptacle is configured to host the implantable enclosure;
    connecting a pigtail disposed within the Faraday cage housing having a charging coil configured to power the implantable enclosure, wherein the impedance engine and the multiplexer allow a 2-point electrical characteristic measurement of each of the plurality of threads; and
    measuring a 2-point electrical characteristic of each of the plurality of threads to assess the integrity of each of the plurality of threads.

13. The method of claim 12, wherein the characteristic of each of the plurality of threads is a measured parameter of continuity of the electrical path between each of the plurality of threads and the impedance engine.

14. The method of claim 13, wherein the measured parameter is selected from the group consisting of impedance, voltage and amperage.

15. The method of claim 14, wherein the measured parameter is impedance.

16. The method of claim 15, wherein impedance is measured in the range of 50 Hz to 5 kHz.

17. The apparatus of claim 15, wherein impedance is measured in the range of 500 Hz to 2 kHz.

18. The method of claim 12, wherein the receptacle within the housing comprises a slot for holding a liquid bath.

19. The method of claim 18, further comprising a liquid.

20. The method of claim 18, wherein the liquid has a concentration of about is 0.1M to about 1M.

21. The method of claim 12, wherein the slot is configured to host the plurality of threads.

* * * * *